United States Patent

Matsubara et al.

(10) Patent No.: US 11,756,190 B2
(45) Date of Patent: Sep. 12, 2023

(54) CELL IMAGE EVALUATION DEVICE, METHOD, AND PROGRAM

(71) Applicant: FUJIFILM Corporation, Tokyo (JP)

(72) Inventors: Kenta Matsubara, Ashigarakami-gun (JP); Takashi Wakui, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/543,301

(22) Filed: Aug. 16, 2019

(65) Prior Publication Data

US 2019/0370967 A1 Dec. 5, 2019

Related U.S. Application Data

(63) Continuation of application No. PCT/JP2018/008085, filed on Mar. 2, 2018.

(30) Foreign Application Priority Data

Mar. 30, 2017 (JP) ................................ 2017-067954

(51) Int. Cl.
    *G06T 7/00* (2017.01)
(52) U.S. Cl.
    CPC .. *G06T 7/0012* (2013.01); *G06T 2207/10056* (2013.01); *G06T 2207/20081* (2013.01);
    (Continued)
(58) Field of Classification Search
    CPC ......... G06T 7/0012; G06T 2207/10056; G06T 2207/20081; G06T 2207/30024;
    (Continued)

(56) References Cited

U.S. PATENT DOCUMENTS

| | | | |
|---|---|---|---|
| 2006/0078218 A1* | 4/2006 | Igarashi | H04N 5/23248 |
| | | | 382/255 |
| 2012/0275671 A1 | 11/2012 | Eichhorn et al. | |

(Continued)

FOREIGN PATENT DOCUMENTS

| | | |
|---|---|---|
| JP | 5-49467 A | 3/1993 |
| JP | 2010-231695 A | 10/2010 |

(Continued)

OTHER PUBLICATIONS

European Communication pursuant to Article 94(3) EPC for corresponding European Application No. 18777272.8, dated Jul. 9, 2020.

(Continued)

*Primary Examiner* — John Villecco
*Assistant Examiner* — Han Hoang
(74) *Attorney, Agent, or Firm* — Birch, Stewart, Kolasch & Birch, LLP

(57) ABSTRACT

Provided are a cell image evaluation device, method, and program which are capable of more accurate and high reliable evaluation even though a captured image of each part to be observed within a container deteriorates. The cell image evaluation device includes an image evaluation unit that evaluates a state of a cell included in a captured image obtained by capturing an inside of the container that contains the cell based on the captured image, and a deterioration determination unit that determines whether or not the captured image deteriorates. The image evaluation unit changes an evaluation method of the captured image according to a determination result of the deterioration determination unit.

12 Claims, 7 Drawing Sheets

(52) U.S. Cl.
CPC .............. *G06T 2207/30024* (2013.01); *G06T 2207/30168* (2013.01)

(58) Field of Classification Search
CPC ......... G06T 2207/30168; G06T 7/0002; G06T 1/00; G06T 3/403; G06T 7/11; C12M 1/00; C12M 1/34; G01N 33/48; G01N 33/483
See application file for complete search history.

(56) References Cited

U.S. PATENT DOCUMENTS

| | | | |
|---|---|---|---|
| 2013/0011036 A1 | 1/2013 | Marugame et al. | |
| 2014/0064594 A1* | 3/2014 | Sugiyama | G02B 21/14 382/133 |
| 2015/0055844 A1 | 2/2015 | Molin et al. | |
| 2015/0187077 A1* | 7/2015 | Ozaki | G06T 7/73 382/133 |
| 2016/0160170 A1 | 6/2016 | Matsubara | |
| 2017/0081628 A1 | 3/2017 | Matsubara | |
| 2017/0186173 A1* | 6/2017 | Hakamada | G06T 7/194 |
| 2018/0032787 A1* | 2/2018 | Iga | C12M 1/00 |
| 2018/0040127 A1* | 2/2018 | Kanda | A61B 1/000094 |
| 2018/0210185 A1* | 7/2018 | Kato | G02B 21/367 |
| 2020/0034651 A1* | 1/2020 | Lesniak | G06T 5/002 |
| 2020/0239823 A1* | 7/2020 | Tanabe | C12M 1/00 |
| 2020/0294203 A1* | 9/2020 | Ikeda | G06T 5/20 |

FOREIGN PATENT DOCUMENTS

| | | |
|---|---|---|
| JP | 2011-210156 A | 10/2011 |
| JP | 2013-535048 A | 9/2013 |
| JP | 2015-61522 A | 4/2015 |
| WO | WO 2015/182382 A1 | 12/2015 |
| WO | WO 2016/120441 A2 | 8/2016 |
| WO | WO 2007/170656 A1 | 10/2016 |

OTHER PUBLICATIONS

Bray et al., "Workflow and Metrics for Image Quality Control in Large-Scale High-Content Screens," Journal of Biomolecular Screening, vol. 17, No. 2, 2011, pp. 266-274.
Extended European Search Report for European Application No. 18777272.8, dated Jan. 13, 2020.
Lou et al., "Quality Classification of Microscopic Imagery with Weakly Supervised Learning," Machine Learning in Medical Imaging, Oct. 1, 2012, pp. 176-183.
Lupica et al., "Hybrid Image Processing Technique for the Robust Identification of Unstained Cells in Bright-Field Microscope Images," International Conference on Computational Intelligence for Modelling Control and Automation, Dec. 10, 2008, pp. 1053-1058.
Japanese Office Action dated Apr. 21, 2020, for corresponding Japense Application No. 2019-509060, with English translation.
International Preliminary Report on Patentability and Written Opinion of the International Searching Authority(Forms PCT/IB/326, PCT/IB/373 and PCTISA/237), dated Oct. 10, 2019, for International Application No. PCT/JP2018/008085, with an English Translation.
International Search Report (Fom PCT/ISA/210), dated Jun. 5, 2018, for International Application No. PCT/JP2018/008085, with an English translation.
European Office Action dated Oct. 22, 2020 for corresponding Application No. 18 777 272.8.
Korean Office Action dated Oct. 23, 2020 for corresponding Application No. 10-2019-7024431 along with an English translation.
Khan, et al., "A Benchmark Data Set to Evaluate the Illumination Robustness of Image Processing Algorithms for Object Segmentation and Classification", PLOS ONE, vol. 10, No. 7, Jul. 20, 2015, pp. 1-9, XP055783063.
Office Action dated Mar. 19, 2021 in corresponding European Patent Application No. 18 777 272.8.
European Communication pursuant to Article 94(3) EPC for corresponding European Application No. 18777272.8, dated Jul. 12, 2021.

* cited by examiner

CELL IMAGE EVALUATION DEVICE, METHOD, AND PROGRAM

CROSS-REFERENCE TO RELATED APPLICATIONS

This application is a Continuation of PCT International Application No. PCT/JP2018/008085 filed on Mar. 2, 2018, which claims priority under 35 U.S.C § 119(a) to Japanese Patent Application No. 2017-067954 filed on Mar. 30, 2017. Each of the above application(s) is hereby expressly incorporated by reference, in its entirety, into the present application.

BACKGROUND OF THE INVENTION

1. Field of the Invention

The present invention relates to a cell image evaluation device, method, and program which evaluate a state of a cell included in a captured image by using the captured image obtained by capturing the cell.

2. Description of the Related Art

Pluripotent stem cells such as embryonic stem (ES) cells and induced pluripotent stem (iPS) cells have ability to differentiate into cells of various tissues, and have received attention as being applicable to regenerative medicine, drug development, and elucidation of diseases.

Meanwhile, a method of evaluating a differentiated state of the cells by capturing the pluripotent stem cells such as the ES cells and the iPS cells or differentiated and induced cells by using a microscope and catching features of an image thereof has been suggested in the related art.

Meanwhile, in order to obtain a high-magnification and wide-field image in a case of capturing the cell by using the microscope as state above, so-called tiling capturing for obtaining has been suggested. Specifically, for example, a method in which parts to be observed within a well are scanned by moving a stage on which a well plate is placed with respect to an image forming optical system, images of the parts to be observed are captured, and then the images of the parts to be observed are connected has been suggested.

SUMMARY OF THE INVENTION

In this case, autofocus control is performed in each part to be observed in a case of scanning and capturing the parts to be observed within the well as stated above. However, an optimal focus position may not be obtained in all the parts to be observed. An error may occur in the autofocus control, and the captured images of some parts to be observed may be blurred images. For example, a light amount of illumination light may fluctuate due to a voltage fluctuation applied to a light source of a microscope device, and the captured image may be a dark image.

Since an image of each cell is not able to be extracted with high accuracy for the deteriorated captured image such as the blurred image and the dark image, for example, in a case where evaluation is performed by using a feature value indicating the state of each cell, accuracy of an evaluation result becomes low, and thus, an evaluation result of which reliability is low may be obtained. That is, in a case where the deteriorated captured image and the undeteriorated captured image are similarly evaluated, accurate evaluation results may not be able to be obtained.

JP2013-535048A suggests that an image of a digital microscope slide is divided into a plurality of regions, only a divided image having appropriate brightness or contrast is evaluated in a case of evaluating quality of each region, and a score of the entire slide is calculated. However, in a case where a divided image having no appropriate brightness or contrast is not evaluated at all, since information of the divided image is completely lost, accuracy may become low as the evaluation of the entire slide.

The present invention has been made in view of the aforementioned problems, and an object of the present invention is to provide a cell image evaluation device, method, and program which are capable of performing more accurate and high reliable evaluation even though a captured image of each part to be observed within a container deteriorates.

A cell image evaluation device according to an aspect of the present invention comprises an image evaluation unit that evaluates a state of a cell included in a captured image obtained by capturing an inside of a container that contains the cell based on the captured image, and a deterioration determination unit that determines whether or not the captured image deteriorates. The image evaluation unit changes an evaluation method of the captured image according to a determination result of the deterioration determination unit.

In the cell image evaluation device according to the aspect of the present invention, the image evaluation unit may evaluate the captured image by an evaluation method which is relatively resistant to deterioration in a case where it is determined that the captured image deteriorates, and may evaluate the captured image by an evaluation method which is relatively weak to the deterioration in a case where it is determined that the captured image does not deteriorate.

In the cell image evaluation device according to the aspect of the present invention, the image evaluation unit may evaluate the captured image by using a feature value indicating the state of the cell included in the captured image in a case where it is determined that the captured image does not deteriorate, and may evaluate the captured image by using an image feature value in a case where it is determined that the captured image deteriorates.

In the cell image evaluation device according to the aspect of the present invention, the feature value indicating the state of the cell may include at least one of a feature value of a state of each cell, a feature value of nucleolus included in the cell, a feature value of white streaks, a feature value of nucleus included in the cell, or a nucleocytoplasmic ratio (NC ratio) of the cell.

In the cell image evaluation device according to the aspect of the present invention, the deterioration determination unit may determine whether or not the captured image is blurred.

In the cell image evaluation device according to the aspect of the present invention, the deterioration determination unit may comprise a blur discriminator that determines whether or not the captured image is blurred, and the blur discriminator may be generated by machine learning.

In the cell image evaluation device according to the aspect of the present invention, the blur discriminator may determine whether or not the captured image is blurred based on at least one of a dispersion of luminance, a contrast, or a set of a minimum value and a maximum value of the captured image.

In the cell image evaluation device according to the aspect of the present invention, the deterioration determination unit may comprise a region discriminator that determines whether the captured image is an image obtained by capturing a cell region or an image obtained by capturing a culture medium region, and in a case where the region discriminator determines that the captured image is the image obtained by capturing the cell region and the blur discriminator determines that the captured image is blurred, the deterioration determination unit may determine that the captured image deteriorates.

In the cell image evaluation device according to the aspect of the present invention, the deterioration determination unit may determine whether or not the captured image is an image deteriorated by fluctuation of a light amount of illumination light.

In the cell image evaluation device according to the aspect of the present invention, the deterioration determination unit may comprise a light amount fluctuation deterioration discriminator that determines whether or not the captured image is the image deteriorated by the fluctuation of the light amount of illumination light, and the light amount fluctuation deterioration discriminator may be generated by machine learning.

In the cell image evaluation device according to the aspect of the present invention, the light amount fluctuation deterioration discriminator may determine whether or not the captured image is the image deteriorated by the fluctuation of the light amount based on at least one of an average luminance or a set of a minimum value and a maximum value of the captured image.

In the cell image evaluation device according to the aspect of the present invention, the image evaluation unit may integrate evaluation results of a plurality of the captured images obtained by capturing the inside of the container, and may calculate an evaluation result for the container.

In the cell image evaluation device according to the aspect of the present invention, the captured image may be an image obtained by capturing each part to be observed within the container by moving at least one of a stage on which the container is placed or an image forming optical system that forms an image of the cell within the container, and the deterioration determination unit may determine whether or not the captured image of each part to be observed deteriorates.

A cell image evaluation method according to another aspect of the present invention comprises determining whether or not a captured image obtained by capturing an inside of a container that contains a cell deteriorates, and changing an evaluation method of the captured image according to a determination result of the deterioration in a case of evaluating a state of the cell included in the captured image based on the captured image.

A cell image evaluation program according to still another aspect of the present invention causes a computer to function as an image evaluation unit that evaluates a state of a cell included in a captured image obtained by capturing an inside of a container that contains the cell based on the captured image, and a deterioration determination unit that determines whether or not the captured image deteriorates. The image evaluation unit changes an evaluation method of the captured image according to a determination result of the deterioration determination unit.

In accordance with the cell image evaluation device, method, and program according to the embodiment of the present invention, it is determined whether the captured image obtained by capturing the inside of the container that contains the cell deteriorates, and the deteriorated captured image and the undeteriorated captured image are evaluated by different evaluation methods in a case of evaluating the state of the cell included in the captured image. Accordingly, it is possible to perform more accurate and high reliable evaluation by evaluating the image by the evaluation method suitable for the image even though the captured image is the deteriorated image.

DESCRIPTION OF THE PREFERRED EMBODIMENTS

Figure 1:
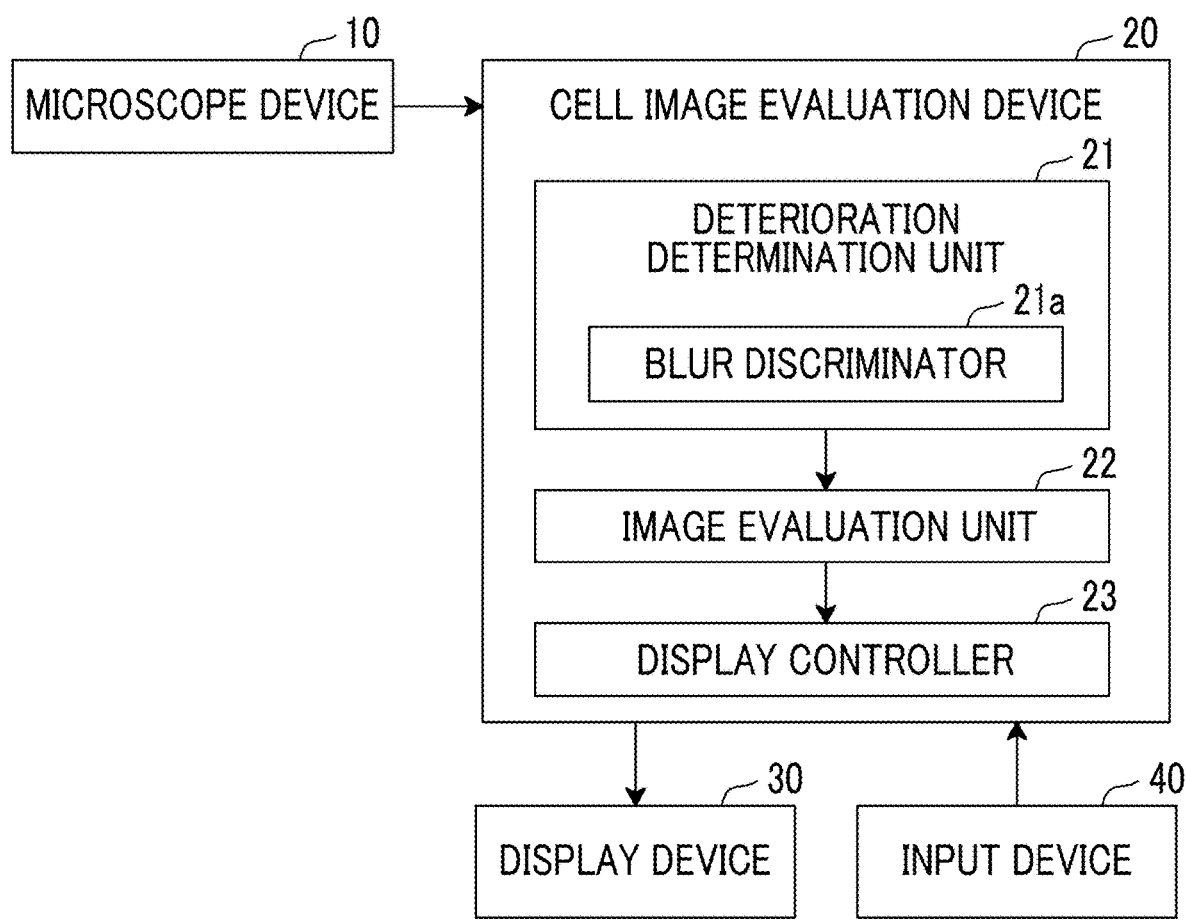
FIG. 1 is a block diagram showing a schematic configuration of a cell image evaluation system using an embodiment of a cell image evaluation device of the present invention.

Hereinafter, a cell image evaluation system using embodiments of a cell image evaluation device, method, and program according to an embodiment of the present invention will be described in detail with reference to the drawings. FIG. 1 is a block diagram showing a schematic configuration of the cell image evaluation system according to the embodiment of the present invention.

As shown in FIG. 1, the cell image evaluation system according to the present embodiment comprises a microscope device 10, a cell image evaluation device 20, a display device 30, and an input device 40.

The microscope device 10 captures cells contained in a culture container, and outputs a captured image. In the present embodiment, specifically, a phase difference microscope device comprising an imaging element such as a charge-coupled device (CCD) image sensor or a complementary metal-oxide semiconductor (CMOS) image sensor is used. As the imaging element, an imaging element in which red, green, and blue (RGB) color filters are provided may be used, or a monochrome imaging element may be used. A phase difference image of the cells contained in the culture container is formed on the imaging element, and the phase difference image is output as the captured image from the imaging element. The microscope device 10 is not limited to the phase difference microscope device, and other microscope devices such as a differential interference microscope device and a bright-field microscope device may be used.

The capturing targets may be a cell colony in which a plurality of cells is aggregated or a plurality of cells which is dispersedly distributed. The cells as the capturing targets are cells of the captured pluripotent stem cells such as iPS cells and ES cells, cells of nerve, skin, cardiac muscle, and liver differentiated and induced from stem cells, and cells and cancer cells of organs obtained from the human body.

In the present embodiment, a well plate with multiple wells is used as the culture container. In a case where the well plate is used, each well corresponds to the container according to the embodiment of the present invention. The microscope device 10 comprises a stage at which the well plate is provided. The stage moves in an X direction and a Y direction perpendicular within a horizontal plane. Parts to be observed within the wells of the well plate are scanned due to the movement of the stage, and thus, cell images for the parts to be observed are captured. The captured image of each part to be observed is output to the cell image evaluation device 20.

Figure 2:
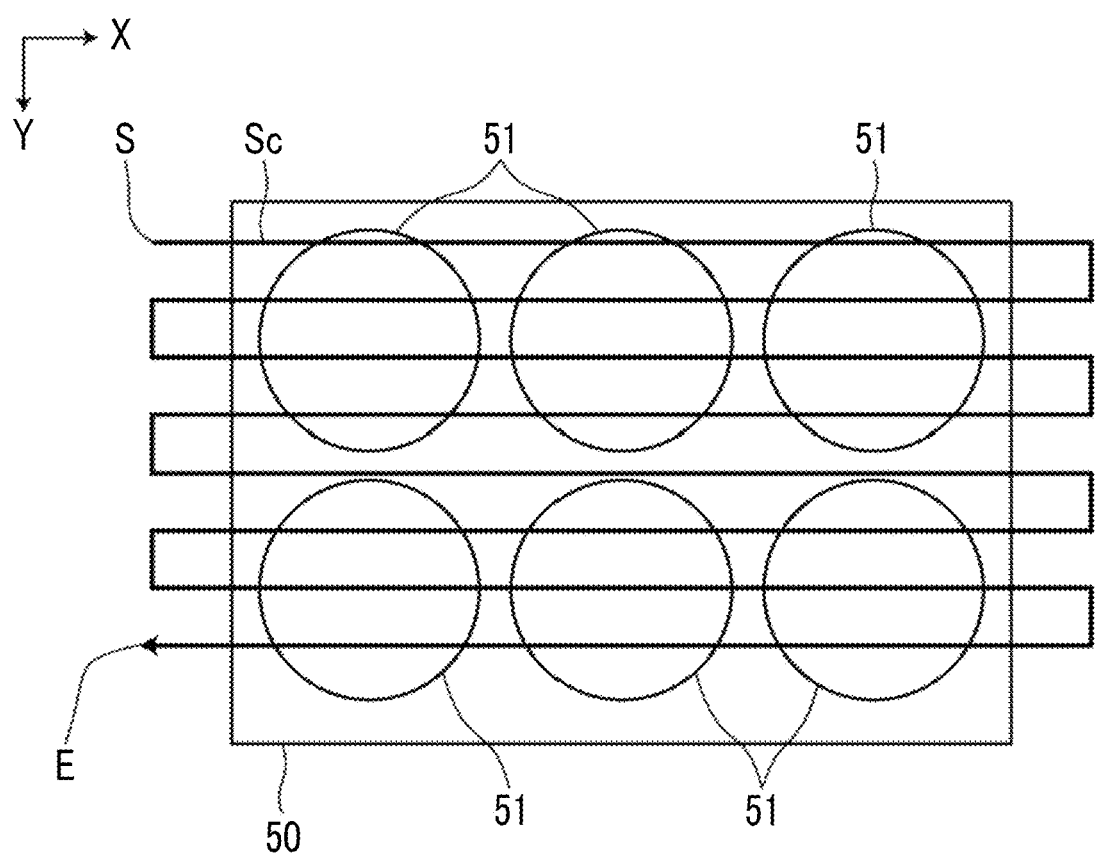
FIG. 2 is a diagram showing a scanning locus of each part to be observed in a well plate.

FIG. 2 is a diagram showing an example in which a scanning locus of each part to be observed is expressed by using a solid line Sc in a case where a well plate 50 having six wells 51 is used. As shown in FIG. 2, each part to be observed within the well plate 50 is scanned along a solid line Sc from a scanning start point S to a scanning end point E due to the movement of the stage in the X direction and the Y direction.

In the present embodiment, autofocus control is performed in each part to be observed within the well by moving the stage or an image forming optical system that forms a phase difference image of the cell on the imaging element in a perpendicular direction.

Although it has been described in the present embodiment that the captured image of each part to be observed within the well is captured by moving the stage, the present invention is not limited thereto. The captured image of each part observed may be captured by moving the image forming optical system toward the stage. Alternatively, both the stage and the image forming optical system may move.

Although the well plate is used in the present embodiment, the container in which the cell is contained is not limited thereto. For example, other containers such as petri dishes or dishes may be used.

As shown in FIG. 1, the cell image evaluation device 20 comprises a deterioration determination unit 21, an image evaluation unit 22, and a display controller 23. The cell image evaluation device 20 is a computer comprising a central processing unit, a semiconductor memory, and a hard disk, and an embodiment of a cell image evaluation program according to the present invention is installed in a hard disk. The cell image evaluation program is executed by the central processing unit, and thus, the deterioration determination unit 21, the image evaluation unit 22, and the display controller 23 shown in FIG. 1 function. Although it has been described in the present embodiment that the functions of the units are performed by the cell image evaluation program, the present invention is not limited thereto. For example, the functions of the units may be performed by appropriately combining a plurality of integrated circuits (ICs), a processor, an application specific integrated circuit (ASIC), a field-programmable gate array (FPGA), and a memory. The cell image evaluation program may be stored in a non-transitory computer-readable recording medium, and may be read into a computer constituting the cell image evaluation device 20. The cell image evaluation program may be distributed via a network.

The deterioration determination unit 21 determines whether the captured image of each part to be observed which is captured by the microscope device 10 deteriorates. Specifically, the deterioration determination unit 21 of the present embodiment includes a blur discriminator 21a. The blur discriminator 21a determines whether or not the captured image is blurred, and thus, the deterioration determination unit 21 determines whether or not the captured image deteriorates. The deterioration determination unit 21 will be described in detail.

The image evaluation unit 22 obtains the captured image of each part to be observed, and evaluates the state of the cell included in the captured image. For example, a case where the state of the cell is evaluated means that the image evaluation unit evaluates whether the cells included in the captured image are undifferentiated cells or differentiated cells, counts the number of cells for each kind of the cell in a case of co-culturing, evaluates percentages of the undifferentiated cells and the differentiated cells included in the captured image, evaluates a growth rate of the cell or the cell colony, or evaluates a reduction rate of cancer cells by anticancer drugs. Here, the evaluation of the state of the cell is not limited thereto, and other evaluation methods may be used.

The image evaluation unit 22 evaluates the state of the cell by different evaluation methods for a blurred captured image and an unblurred captured image. Specifically, the image evaluation unit 22 evaluates the unblurred captured image by using the feature value indicating the state of the cell included in the captured image, and evaluates the blurred captured image by using an image feature value. The image evaluation using the image evaluation unit 22 will be described in detail.

Figure 4:
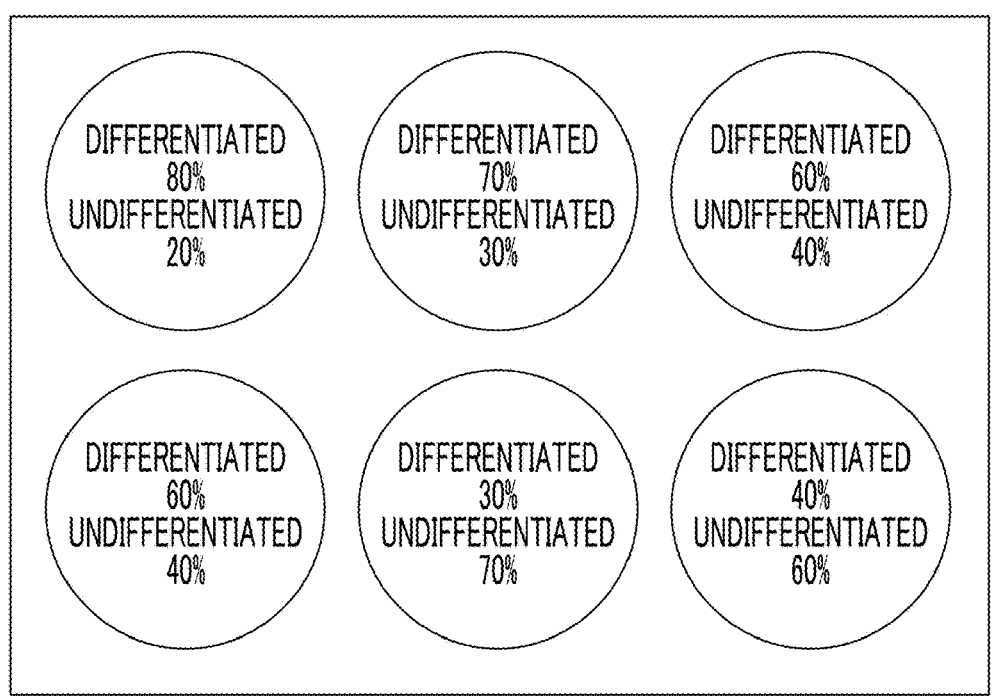
FIG. 4 is a diagram showing a display example of an evaluation result integrated for the wells.

The display controller 23 displays the evaluation result using the image evaluation unit 22 on the display device 30. Specifically, in the present embodiment, since the evaluation result of each well is calculated by the image evaluation unit 22, the display controller 23 displays the evaluation result of each well on the display device 30. FIG. 4 shows an example in which the percentage of the differentiated cells and the percentage of the undifferentiated cells of each well are calculated and the calculation result is displayed as the integrated evaluation result in a case where the well plate has six wells. In the example of FIG. 4, 80% of differentiated cells and 20% of undifferentiated cells are present in an upper left well. 70% of differentiated cells and 30% of undifferentiated cells are present in an upper central well. 60% of differentiated cells and 40% of undifferentiated cells are present in an upper right well. 60% of differentiated cells and 40% of undifferentiated cells are present in a lower left well. 30% of differentiated cells and 70% of undifferentiated cells are present in a lower central well. 40% of differentiated cells and 60% of undifferentiated cells are present in a lower right well.

The display controller 23 generates a combination image by connecting the captured images of the parts to be observed, and displays the combination image on the display device 30.

The display device 30 comprises, for example, a liquid crystal display that displays the evaluation result using the image evaluation unit 22 and the combination image generated by the display controller 23 as stated above. The display device 30 may be a touch panel, and may also serve as the input device 40.

The input device 40 comprises a mouse or a keyboard, and receives various setting inputs from the user.

Figure 3:
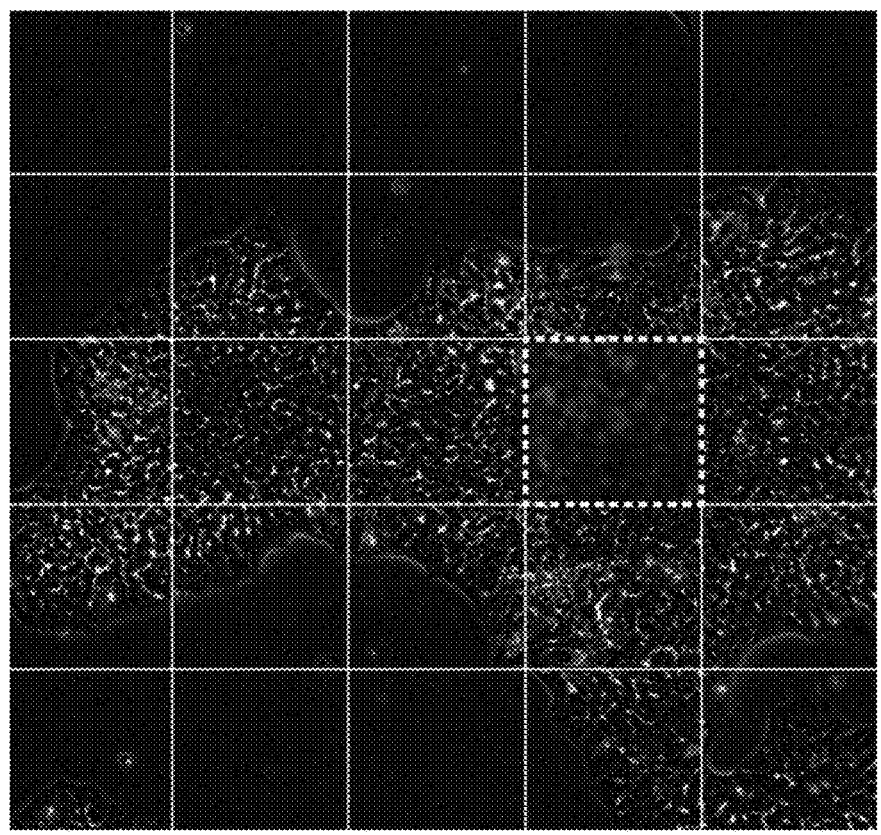
FIG. 3 is a diagram showing an example of a captured image of each part to be observed within the well.

Next, the deterioration determination unit 21 will be described in detail. Although it has been described in the present embodiment that each part to be observed within the well is scanned and the autofocus control is performed in each part to be observed as stated above, an optimal focus position may not be obtained in all the parts to be observed. An error may occur in the autofocus control, and the captured images of some parts to be observed may be the blurred images. In a case where the blurred captured image is evaluated similarly to other unblurred captured images, an accurate evaluation result may not be obtained. FIG. 3 is a diagram showing an example of the captured image of each part to be observed within the well. In FIG. 3, each divided region in a rectangular region corresponds to each part to be observed. In the example shown in FIG. 3, the captured image of the part to be observed which is indicated by a dotted square is the blurred image.

In the cell image evaluation system of the present embodiment, the deterioration determination unit 21 determines whether or not the captured image of each part to be observed is blurred, and changes the evaluation method according to the determination result.

Specifically, the blur discriminator 21a inputs at least one of a dispersion of luminance, a contrast, or a set of a minimum value and a maximum value of the blurred captured image and the unblurred captured image, and generates, as an output, a determination result of whether or not the captured image is blurred through machine learning. Known methods can be used as the machine learning method. Support vector machine (SVM), deep neural network (DNN), convolutional neural network (CNN), recurrent neural network (RNN), and denoising stack auto encoder (DSA) can be used.

The blur discriminator 21a receives an input of the captured image of each part to be observed, and outputs a determination result of whether or not the captured image is blurred.

Although it has been described in the present embodiment that the blur discriminator 21a on which the machine learning is performed determines whether or not the captured image is blurred as stated above, the determination method is not limited thereto. For example, an edge may be detected from the captured image, and the determination may be performed based on the amount of edges. Alternatively, the determination may be determined from the set of the maximum value and the minimum value of the luminance, or the determination may be performed by analyzing a spatial frequency component of the captured image.

Next, the image evaluation using the image evaluation unit 22 will be described in detail. It is possible to recognize the image of the cell included in the captured image or the image of the nucleus or nucleolus with high accuracy for the unblurred captured image. Thus, the image evaluation unit 22 evaluates the image by using the feature value indicating the state of the cell as stated above, and thus, it is possible to obtain an evaluation result excellent in biological interpretability. In the present embodiment, the evaluation method using the feature value indicating the state of the cell is an evaluation method which is relatively weak to blurring (deterioration).

At least one of a feature value of state of each cell, a feature value of a nucleolus included in the cell, a feature value of white streaks, a feature value of nucleus included in the cell, or a NC ratio of the cell can be used as the feature value indicating the state of the cell.

Examples of the feature value indicating the state of each cell include the number of cells, the density of cells, an increasing rate of the cells, and a degree of circularity of the cell. However, other feature values may be used as long as each cell included in the captured image is recognized and a feature value is calculated based on the recognized cell. Examples of the method of recognizing the cell included in the captured image include a method of detecting an edge of the image of the cell, a method of detecting the cell by using a pattern matching process, a method of detecting the cell by using a discriminator generated by machine learning. However, other known methods can be used. As for the degree of circularity of the cell, the degree of circularity of the undifferentiated cell becomes relatively high, but the degree of circularity of the differentiated cell becomes relatively low since the differentiated cell has an elongated shape. Accordingly, the image evaluation unit 22 can evaluate whether the cells are the differentiated cells or the undifferentiated cells by calculating the degrees of circularity of each cell. In the pluripotent stem cells, in a case where the cell differentiates, since a chromatin structure in the nucleus changes and becomes dark, it is possible to evaluate whether the cell differentiates or undifferentiates by detecting the nucleus and then evaluating luminance of the nucleus. Here, the method of evaluating whether the cells are the differentiated cells or the undifferentiated cells is not limited thereto, and other known methods can be used. Alternatively, in a case where nerve cells are evaluated, a length of a dendrite can be used as the feature value indicating the state of each cell. It is possible to evaluate a growth rate of the nerve cell by using the length of the dendrite.

Examples of the feature value of the nucleus or nucleolus included in the cell include the number of nuclei or nucleoli, the density of nuclei or nucleoli, and an increasing rate of the nuclei or nucleoli. However, other feature values may be used as long as the nuclei or nucleoli included in the captured image is recognized and a feature value is calculated based on the recognized nuclei or nucleoli. Similarly to the method of recognizing the cell, the edge detection, the detection using the pattern matching, and the detection using the discriminator can be used as the method of recognizing the nuclei or nucleoli included in the captured image.

The white streaks are blurring (halo) of light due to diffracted light generated between the cells and a background. Examples of the feature value of the white streaks include the total area of white streaks, the density of white streaks, and the distribution state of white streaks. However, other feature values may be used as long as the white streaks included in the captured image are recognized and a feature value is calculated based on the recognized white streaks. Examples of the method of recognizing the white streaks include a method of binarizing the captured image and extracting the white streaks through threshold value processing, a method of detecting the white streaks by using a pattern matching process, a method of detecting the white streaks by using a discriminator generated by machine learning. However, other known methods can be used. As for the feature value of the white streaks, for example, the amount of white streaks is small in a state in which the number of undifferentiated cells is large within the cell colony, but the number of white streaks is large in a case where the differentiation progresses and the number of differentiated cells is large. Accordingly, it is possible to evaluate a degree of differentiation or a degree of undifferentiation of the cell colony or a growth rate of the cell colony based on the feature value of the white streaks.

The NC ratio of the cell is an area ratio of the nucleus to the cytoplasm. It is possible to obtain the NC ratio by using detectors of the cytoplasm and the nucleus. In general, the cytoplasm has a gray and flat appearance, whereas the nucleus is relatively round and includes a structure such as the nucleolus therein. Accordingly, a cytoplasm region and a nucleus region are obtained by creating the detectors through machine learning and applying the created detectors to the captured image. It is possible to calculate the NC ratio by calculating an area ratio of the cytoplasm region and the nucleus region obtained in this manner. The NC ratio may be calculated for each cell colony, or the NC ratio within a previously designated region.

Meanwhile, detection accuracy of the image of each cell or the image of the nucleolus becomes low for the blurred captured image. Accordingly, evaluation accuracy in a case where the evaluation is performed by using the image feature value of the captured image itself is more improved than evaluation accuracy in a case where the evaluation is performed by using the feature value indicating the state of each cell like the unblurred captured image. In the present embodiment, the evaluation method using the image feature value is an evaluation method which is relatively more resistant to blurring (deterioration) than the evaluation method using the feature value indicating the state of the cell.

The image feature value used in a case of evaluating the blurred captured image is a feature value of the captured image itself. Specifically, average luminance of the captured image, a dispersion of the luminance of the captured image, a difference between a maximum value and a minimum value of the luminance of the captured image, a contrast of the captured image, entropy of the captured image, a spatial frequency distribution of the captured image, directivity of the captured image, and a Zernike feature of the captured image may be used.

As the method of evaluating the state of the cell included in the captured image by using such an image feature value, for example, a relationship between the image feature value and the evaluation result corresponding to the image feature value may be obtained in advance through an experiment, and the evaluation result may be obtained based on the relationship between the image feature value of the captured image and the evaluation result. An evaluator may be generated by learning the relationship between the image feature value and the evaluation result corresponding to the image feature value through, for example, machine learning, and the evaluation result may be obtained by inputting the image feature value of the captured image to the evaluator.

The image evaluation unit 22 of the present embodiment integrates the evaluation results of the captured images of the parts to be observed within the well, and calculates the evaluation result for the well. That is, the evaluation result of each well is calculated. It is possible to manage the cells of each well in a case of passaging or shipping of the cells by calculating the evaluation result of each well (each container) as stated above.

In the present embodiment, since the state of the cell is evaluated by different evaluation methods for the blurred captured image and the unblurred captured image as stated above, it is possible to evaluate the captured image of each part to be observed by an appropriate evaluation method, and it is possible to obtain a more accurate and reliable evaluation result as the evaluation result of each well.

Specifically, for example, the percentage of the differentiated cells and the percentage of the undifferentiated cells for each well may be obtained by calculating average values of the percentages of the differentiated cells and the percentages of the undifferentiated cells included in the captured images of the parts to be observed within the well.

Alternatively, in a case where the growth rate of the cell or the cell colony is evaluated for the captured image of each part to be observed within the well, an average value of the growth rates of the part to be observed may be obtained as a growth rate of each well. A percentage of the number of parts to be observed, of which the growth rate is equal to or greater than a threshold value, to the number of all parts to be observed within the well may be calculated, and this percentage may be obtained as the growth rate of each well. Alternatively, the evaluation result of each well may be "good" in a case where this percentage is equal to or greater than the threshold value, and the evaluation result of each well may be "poor" in a case where this percentage is less than the threshold value. Alternatively, the evaluation result of the part to be observed, of which the growth rate is equal to or greater than the threshold value, may be "good", and the evaluation result of the part to be observed, of which the growth rate is less than the threshold value, may be "poor". Further, the evaluation result of each well may be "good" in a case where the number of parts to be observed, of which the evaluation result is "good" is equal to or greater than a threshold value, and the evaluation result of each well may be "poor" in a case where the number of parts to be observed of which the evaluation result is "good" is less than the threshold value.

Figure 5:
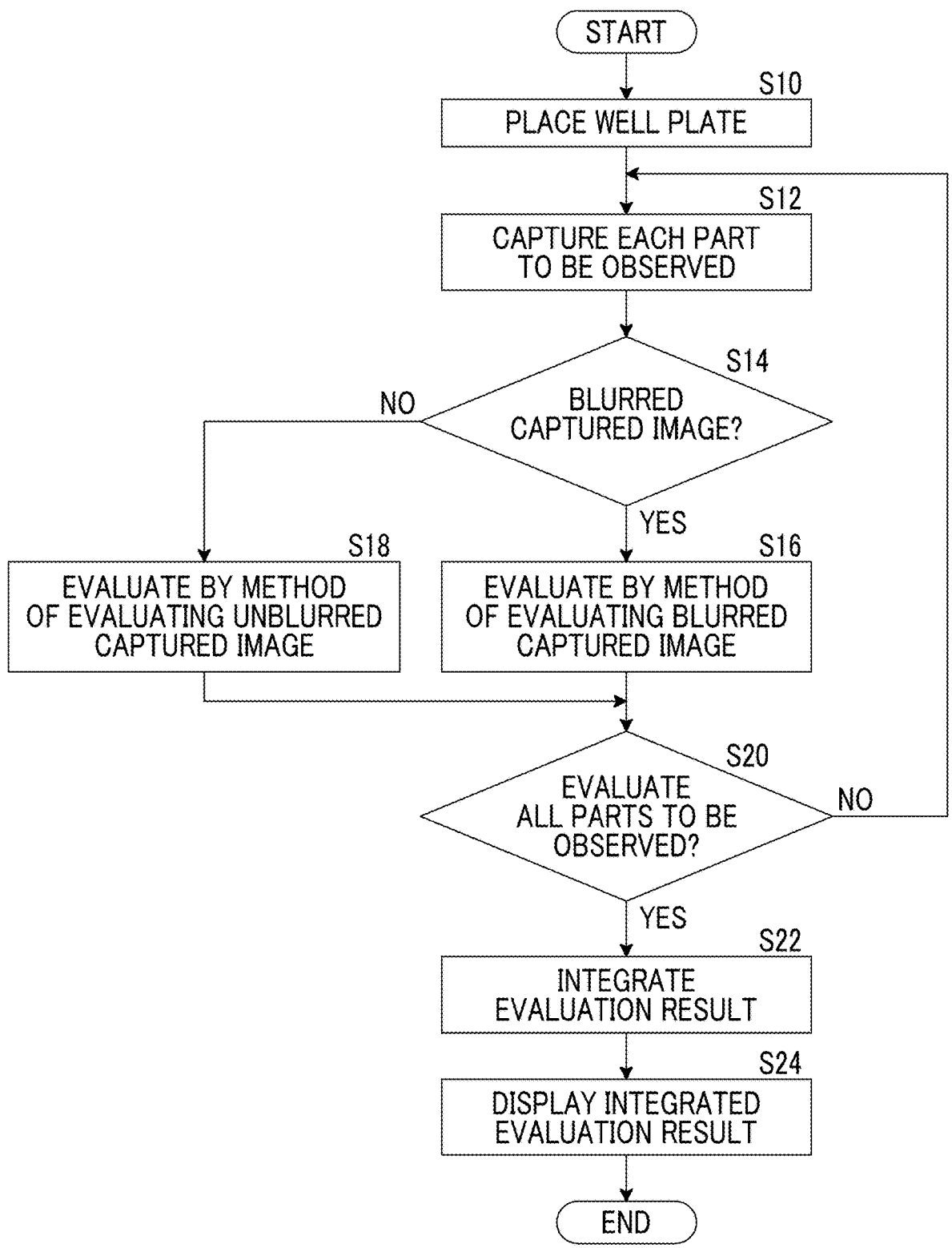
FIG. 5 is a flowchart for describing an operation of the cell image evaluation system using the cell image evaluation device according to the embodiment of the present invention.

Next, an operation of the cell image evaluation system of the present embodiment will be described with reference to a flowchart shown in FIG. 5.

Initially, the well plate that contains the cells and the culture solution is placed on the stage of the microscope device 10 (S10). The parts to be observed within each well of the well plate are scanned while moving the stage in the X direction and the Y direction, and thus, the captured images of the parts to be observed are captured (S12).

The captured images of the parts to be observed which are captured in the microscope device 10 are sequentially output to the cell image evaluation device 20, and are sequentially input to the deterioration determination unit 21 and the display controller 23 (S12). The deterioration determination unit 21 determines whether the input captured image of the part to be observed is the blurred captured image or the unblurred captured image (S14).

In a case where the deterioration determination unit 21 determines that the captured image is the blurred captured image, the image evaluation unit 22 evaluates the captured image by using the method of evaluating the blurred captured image (S16). Specifically, the image feature value is calculated for the captured image, and the state of the cell included in the captured image is evaluated by using the image feature value.

Meanwhile, in a case where the deterioration determination unit 21 determines that the captured image is the unblurred captured image, the image evaluation unit 22 evaluates the captured image by using the method of evaluating the unblurred captured image (S18). Specifically, the feature value indicating the state of the cell is calculated for the captured image, and the state of the cell included in the captured image is evaluated by using the feature value.

The processing of S12 to S18 is repeated until all the parts to be observed are scanned and the evaluation of the captured images of all the parts to be observed is ended (S20, NO).

In a case where the evaluation of the captured images of all the parts to be observed is ended (S20, YES), the image evaluation unit 22 integrates the evaluation results of the captured images of the parts to be observed, and obtains the evaluation result of each well (S22).

The display controller 23 generates the combination image by using the captured images of the parts to be observed, displays the combination image on the display device 30, and displays the integrated evaluation result of each well on the display device 30 (S24).

According to the cell image evaluation system of the embodiment, since the blurred captured image and the unblurred captured image are evaluated by different evaluation methods in a case of evaluating the state of the cell included in the captured image by determining whether or not the captured image of each part to be observed is blurred, it is possible to evaluate the image by an evaluation method suitable for the captured image, and it is possible to perform more accurate and high reliable evaluation.

Although it has been described in the embodiment that the image evaluation unit 22 integrates the captured images of the parts to be observed within the well and calculates the evaluation result of each well, weights may be added to the evaluation result of the blurred captured image and the evaluation result of the unblurred captured image in a case of calculating the evaluation result integrated in this manner. As for the weight, it is preferable that a weight to be added to the evaluation result of the unblurred captured image is set so as to be larger than a weight to be added to the evaluation result of the blurred captured image. This is because it is considered that the accuracy of the evaluation result of the unblurred captured image is high.

Specifically, in a case where the average value of the growth rates of the parts to be observed within the well is obtained as the growth rate of each well, a weight of less than 0.5 may be added to the growth rate of the part to be observed of the blurred captured image, and a weight of 0.5 or more may be added to the growth rate of the part to be observed of the unblurred captured image.

Alternatively, in a case where the evaluation result of the part to be observed, of which the growth rate is equal to or greater than the threshold value, is "good" and the evaluation result of the part to be observed, of which the growth rate is less than the threshold value, is "poor", the image may be evaluated as "good" or "poor" by adding the weight of less than 0.5 to the growth rate of the part to be observed of the blurred captured image, and the image may be evaluated as "good" or "poor" by adding the weight of 0.5 or more to the growth rate of the part to be observed of the unblurred captured image. As stated above, the evaluation result of each well may be "good" in a case where the number of parts to be observed, which are included in the well and of which the evaluation result is "good", is equal to or greater than the threshold value, and the evaluation result of each well may be "poor" in a case where the number of parts to be observed, of which the evaluation result is "good", is less than the threshold value.

Although it has been described in the embodiment that the blur discriminator 21a determines whether or not the captured image is blurred, for example, since a luminance distribution of a captured image obtained by capturing a range of a culture medium such as a culture solution among the captured images obtained by capturing the parts to be observed within the well is similar to a luminance distribution of the blurred image, even though this captured image is not blurred, this captured image is likely to be erroneously determined to be the blurred image.

Figure 6:
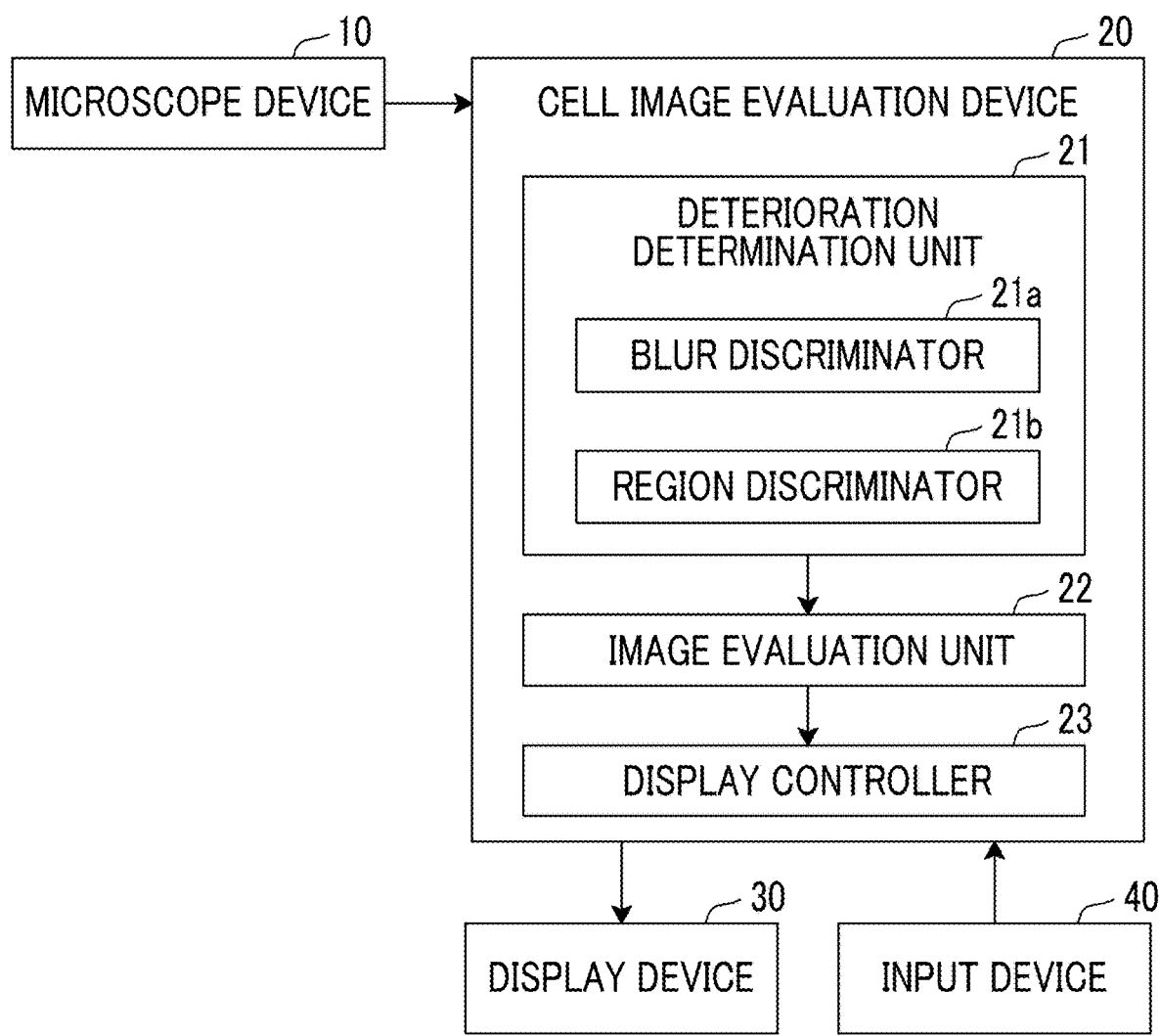
FIG. 6 is a block diagram showing a schematic configuration of a modification example of the cell image evaluation system shown in FIG. 1.

Thus, a region discriminator 21b may be further provided in the deterioration determination unit 21, as shown in FIG. 6. The region discriminator 21b determines whether the captured image is an image obtained by capturing the cell region or an image obtained by capturing a culture medium region.

Specifically, the region discriminator 21b inputs the captured image obtained by capturing the cell region and the captured image obtained by capturing the culture medium region, and generates, as an output, a determination result of whether the captured image is the image obtained by capturing the cell region or the captured image obtained by capturing the culture medium region through machine learning. Similarly to the blur discriminator 21a, known methods can be used as the machine learning method.

The region discriminator 21b receives the input of the captured image of each part to be observed, and outputs the determination result of whether the captured image is the captured image obtained by capturing the cell region or the captured image obtained by capturing the culture medium region.

Although it has been described in the present embodiment that the region discriminator 21b on which the machine learning is performed determines whether the captured image is the captured image obtained by capturing the cell region or the captured image obtained by capturing the culture medium region as stated above, the determination method is not limited thereto. For example, an edge may be detected from the captured image, and the determination may be performed based on the amount of edges. Alternatively, the determination may be determined from the set of the maximum value and the minimum value of the luminance, or the determination may be performed by analyzing a spatial frequency component of the captured image.

In a case where the region discriminator 21b determines that the captured image is the image obtained by capturing the cell region and the blur discriminator 21a determines that the captured image is blurred, it may be determined that the captured image deteriorates, and the evaluation may be performed by using the image feature value. Meanwhile, even though the blur discriminator 21a determines that the captured image is blurred, in a case where the region discriminator 21b determines that the captured image is the image obtained by capturing the culture medium region, the evaluation may be performed by using the feature indicating the state of the cell instead of the image feature value.

Although it has been described in the embodiment that the deterioration determination unit 21 determines whether or not the captured image deteriorates by determining whether the captured image is blurred, that is, determines the deterioration of the captured image due to the error in the autofocus control, a deterioration cause of the captured image is not limited thereto.

Figure 7:
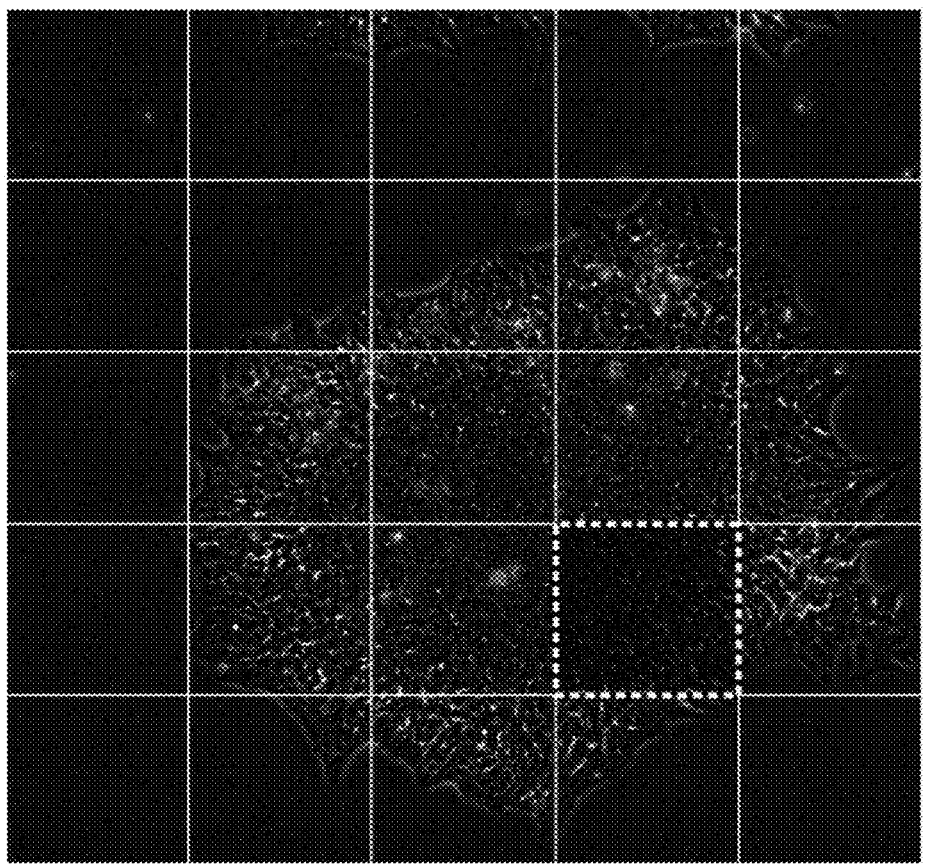
FIG. 7 is a diagram showing an example of a captured image of each part to be observed within the well.

For example, a light amount of illumination light may fluctuate due to a voltage fluctuation applied to a light source of the microscope device 10, and the captured image may be a dark image. In a case where such a dark captured image is evaluated similarly to another captured image having a normal light amount, an accurate evaluation result may not be obtained. FIG. 7 is a diagram showing an example of the captured image of each part to be observed within the well. In FIG. 7, each divided region in a rectangular region corresponds to each part to be observed. In the example shown in FIG. 7, a captured image of each part to be observed which is indicated by a dotted square is an image deteriorated due to the fluctuation of the light amount of illumination light.

Figure 8:
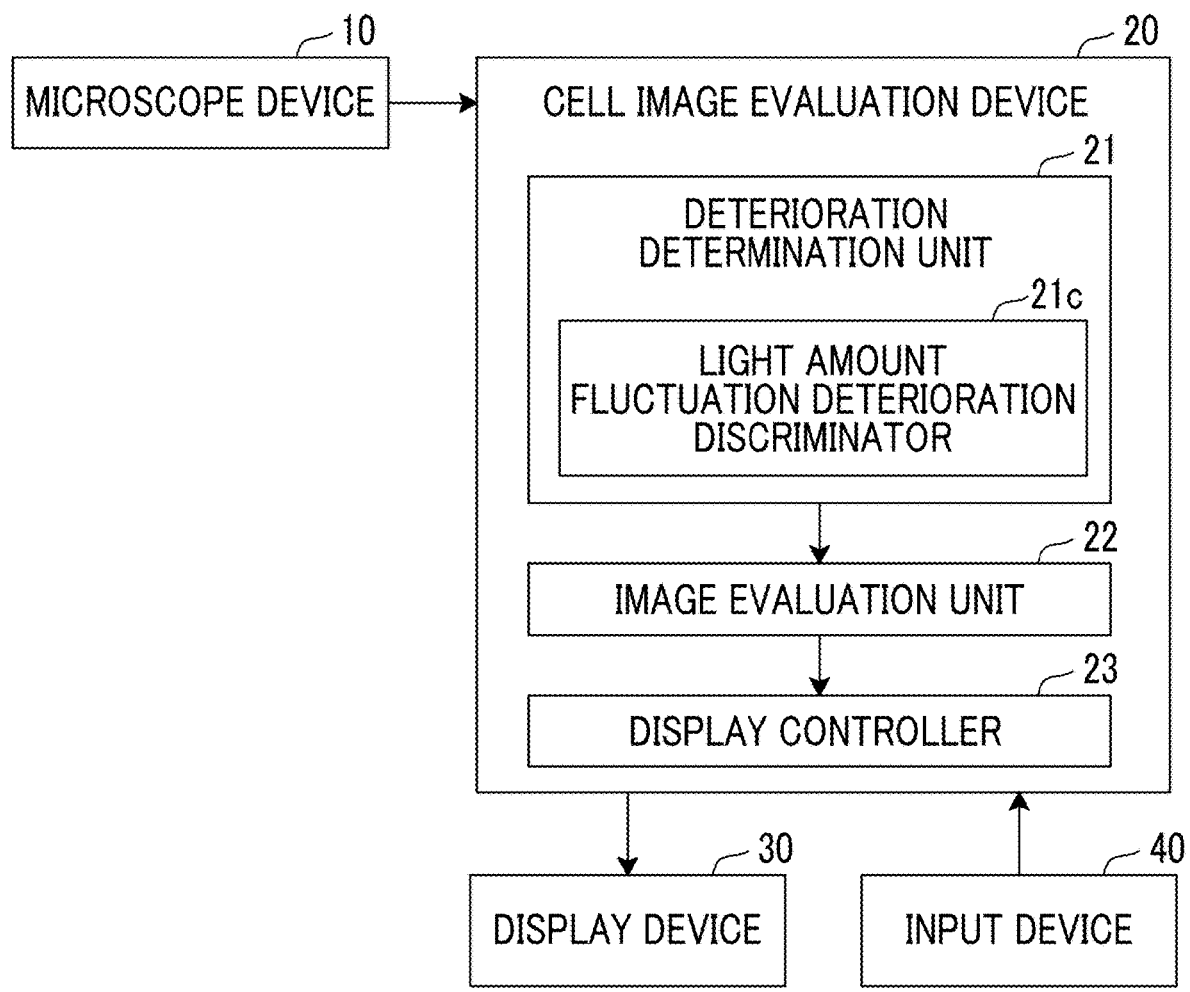
FIG. 8 is a block diagram showing another schematic configuration of a cell image evaluation system using a cell image evaluation device according to the embodiment of the present invention.

Thus, as shown in FIG. 8, a light amount fluctuation deterioration discriminator 21c may be provided in the deterioration determination unit 21. The light amount fluctuation deterioration discriminator 21c may determine whether or not the captured image of each part to be observed deteriorates due to the fluctuation of the light amount of illumination light, and may change the evaluation method according to the determination result.

Specifically, the light amount fluctuation deterioration discriminator 21c inputs at least one of average luminance or the set of the minimum value and the maximum value of the captured image, and generates, as an output, a determination result of whether or not the captured image deteriorates due to the fluctuation of the light amount of illumination light through machine learning. Similarly to the blur discriminator 21a, known methods can be used as the machine learning method.

The light amount fluctuation deterioration discriminator 21c receives the input of the captured image of each part to be observed, and outputs the determination result of whether or not the captured image deteriorates due to the fluctuation of the light amount of illumination light.

Although it has been described in the present embodiment that the light amount fluctuation deterioration discriminator 21c on which the machine learning is performed determines whether or not the captured image deteriorates due to the fluctuation of the light amount as stated above, the determination method is not limited thereto. For example, the determination may be performed by threshold value determination of the average luminance of the captured image. Alternatively, the determination may be determined by analyzing the luminance distribution of the captured image.

In a case where the light amount fluctuation deterioration discriminator 21c determines that the captured image deteriorates due to the fluctuation of the light amount of illumination light, the captured image may be evaluated by using the image feature value. Meanwhile, in a case where the captured image does not deteriorate due to the fluctuation of the light amount of illumination light, the evaluation may be performed by using the feature indicating the state of the cell instead of the image feature value.

The deterioration determination unit 21 may comprise both the blur discriminator 21a and the light amount fluctuation deterioration discriminator 21c, and may further comprise the region discriminator 21b.

EXPLANATION OF REFERENCES

10: microscope device
20: cell image evaluation device
21: deterioration determination unit
21a: blur discriminator
21b: region discriminator
21c: light amount fluctuation deterioration discriminator
22: image evaluation unit
23: display controller
30: display device
40: input device
50: well plate
51: well
E: scanning end point
S: scanning start point
Sc: solid line indicating scanning locus

What is claimed is:

1. A cell image evaluation device comprising:
a processor configured to:
receive a plurality of captured images obtained by capturing divided regions each corresponding to a part to be observed inside a container that contains a cell;
for each of the plurality of captured images:
determine whether or not the captured image is deteriorated;
after it is determined whether or not the captured image is deteriorated, evaluate a state of the cell included in the captured image by applying, to the entire captured image, an evaluation method using a feature value indicating the state of the cell included in the captured image in a case where it is determined that the captured image is not deteriorated, and evaluate the state of the cell included in the captured image by applying, to the entire captured image, an evaluation method using an image feature value in a case where it is determined that the captured image is deteriorated; and
integrate all of evaluation results of the plurality of the captured images obtained by capturing the container, and calculate an evaluation result for the entire container, the calculation including adding different weights to the evaluation result of the captured image determined to be deteriorated and the evaluation result of the captured image determined not to be deteriorated,
wherein the image feature value is at least one of entropy of the captured image or a spatial frequency distribution of the captured image.

2. The cell image evaluation device according to claim 1, wherein the feature value indicating the state of the cell includes at least one of a feature value of a state of each cell, a feature value of nucleolus included in the cell, a feature value of white streaks, a feature value of nucleus included in the cell, or a nucleocytoplasmic ratio of the cell.

3. The cell image evaluation device according to claim 1, wherein the processor is further configured to determine whether or not the captured image is blurred.

4. The cell image evaluation device according to claim 3, wherein the processor is further configured to perform as a blur discriminator that determines whether or not the captured image is blurred, and
the blur discriminator is generated by machine learning.

5. The cell image evaluation device according to claim 4, wherein the blur discriminator determines whether or not the captured image is blurred based on at least one of a dispersion of luminance, a contrast, or a set of a minimum value and a maximum value of the captured image.

6. The cell image evaluation device according to claim 4, wherein the processor is further configured to perform as a region discriminator that determines whether the captured image is an image obtained by capturing a cell region or an image obtained by capturing a culture medium region, and
in a case where the region discriminator determines that the captured image is the image obtained by capturing the cell region and the blur discriminator determines that the captured image is blurred, it is determined that the captured image is deteriorated.

7. The cell image evaluation device according to claim 1, wherein the processor is further configured to determine whether or not the captured image is an image deteriorated by fluctuation of a light amount of illumination light.

8. The cell image evaluation device according to claim 7, wherein the processor is further configured to perform as a light amount fluctuation deterioration discriminator that determines whether or not the captured image is the image deteriorated by the fluctuation of the light amount of illumination light, and
the light amount fluctuation deterioration discriminator is generated by machine learning.

9. The cell image evaluation device according to claim 8, wherein the light amount fluctuation deterioration discriminator determines whether or not the captured image is the image deteriorated by the fluctuation of the light amount based on at least one of an average luminance or a set of a minimum value and a maximum value of the captured image.

10. The cell image evaluation device according to claim 1,
wherein the captured image is an image obtained by capturing each part to be observed within the container by moving at least one of a stage on which the container is placed or an image forming optical system that forms an image of the cell within the container, and
the processor is further configured to determine whether or not the captured image of each part to be observed is deteriorated.

11. A cell image evaluation method of a cell image evaluation device, the method comprising:
receiving a plurality of captured images obtained by capturing divided regions corresponding to a part to be observed inside a container that contains a cell;
for each of the plurality of captured images:
determining whether or not the captured image is deteriorated;
evaluating a state of the cell included in the captured image by applying, to the entire captured image, an evaluation method using a feature value indicating the state of the cell included in the captured image in a case where it is determined that the captured image is not deteriorated, and evaluating the state of the cell included in the captured image by applying, to the entire captured image, an evaluation method using an image feature value in a case where it is determined that the captured image is deteriorated; and
integrating all of evaluation results of the plurality of the captured images obtained by capturing the container, and calculating an evaluation result for the entire container, the calculating including adding different weights to the evaluation result of the captured image determined to be deteriorated and the evaluation result of the captured image determined not to be deteriorated,
wherein the image feature value is at least one of entropy of the captured image or a spatial frequency distribution of the captured image.

12. A non-transitory computer readable recording medium storing a cell image evaluation program causing a computer to function as a cell image evaluation device, the function comprising:
receiving a plurality of captured images obtained by capturing divided regions each corresponding to a part to be observed inside a container that contains a cell;
for each of the plurality of captured images:
determining whether or not the captured image is deteriorated;
evaluating a state of the cell included in the captured image by applying, to the entire captured image, an evaluation method using a feature value indicating the state of the cell included in the captured image in a case where it is determined that the captured image is not deteriorated, and evaluating the state of the cell included in the captured image by applying, to the entire captured image, an evaluation method using an image feature value in a case where it is determined that the captured image is deteriorated; and
integrating all of evaluation results of the plurality of the captured images obtained by capturing the container, and calculating an evaluation result for the entire container, the calculating including adding different weights to the evaluation result of the captured image determined to be deteriorated and the evaluation result of the captured image determined not to be deteriorated,
wherein the image feature value is at least one of entropy of the captured image or a spatial frequency distribution of the captured image.

* * * * *